United States Patent
Lenarz et al.

(10) Patent No.: US 10,881,467 B2
(45) Date of Patent: Jan. 5, 2021

(54) POSITIONING AID FOR SURGICAL PROCEDURES

(71) Applicant: OtoJig GmbH, Hannover (DE)

(72) Inventors: Thomas Lenarz, Hannover (DE); Jan-Philipp Kobler, Engelskirchen (DE); Marcel Kluge, Hannover (DE); Samuel John, Hannover (DE); Tobias Ortmaier, Hemmingen (DE); Omid Majdani, Hannover (DE); Thomas Stephan Rau, Langenhagen (DE)

(73) Assignee: OtoJig GmbH, Hannover (DE)

( * ) Notice: Subject to any disclaimer, the term of this patent is extended or adjusted under 35 U.S.C. 154(b) by 303 days.

(21) Appl. No.: 15/580,383

(22) PCT Filed: Jun. 8, 2015

(86) PCT No.: PCT/DE2015/100227
§ 371 (c)(1),
(2) Date: Dec. 7, 2017

(87) PCT Pub. No.: WO2016/198032
PCT Pub. Date: Dec. 15, 2016

(65) Prior Publication Data
US 2018/0110568 A1    Apr. 26, 2018

(51) Int. Cl.
*A61B 34/20*    (2016.01)
*A61B 34/10*    (2016.01)
(Continued)

(52) U.S. Cl.
CPC .......... *A61B 34/20* (2016.02); *A61B 17/0218* (2013.01); *A61B 17/1771* (2016.11);
(Continued)

(58) Field of Classification Search
CPC ......... A61B 34/20; A61B 34/10; A61B 90/10; A61B 90/11; A61B 17/0218;
(Continued)

(56) References Cited

U.S. PATENT DOCUMENTS

| 7,981,122 B2 | 7/2011 | Labadie et al. |
| 2010/0179564 A1 | 7/2010 | Mitchell et al. |

(Continued)

FOREIGN PATENT DOCUMENTS

| CN | 101 766 505 A | 7/2010 |
| CN | 101 773 410 A | 7/2010 |

(Continued)

OTHER PUBLICATIONS

International Search Report of PCT/DE2015/100227, dated Feb. 15, 2016.
(Continued)

*Primary Examiner* — Diane D Yabut
(74) *Attorney, Agent, or Firm* — Collard & Roe, P.C.

(57) ABSTRACT

A positioning aid for surgical procedures has a carrier system and a template. The carrier system consists of a carrier plate, which is provided with a recess, and supports. The carrier plate can be secured to a cranial bone via the supports over an operating field for the surgical procedure. The template has a template plate which can be connected to the carrier plate in a play-free manner and which comprises a guiding aperture. The guiding aperture is arranged and oriented in the template plate, which consists of a blank, in an individualized manner according to coordinates ascertained in advance. The central longitudinal axis of the guiding aperture matches a trajectory for accessing the operating field for the surgical procedure when the carrier system and the template are assembled and the carrier system is secured to the cranial bone.

10 Claims, 2 Drawing Sheets

Figure 1:
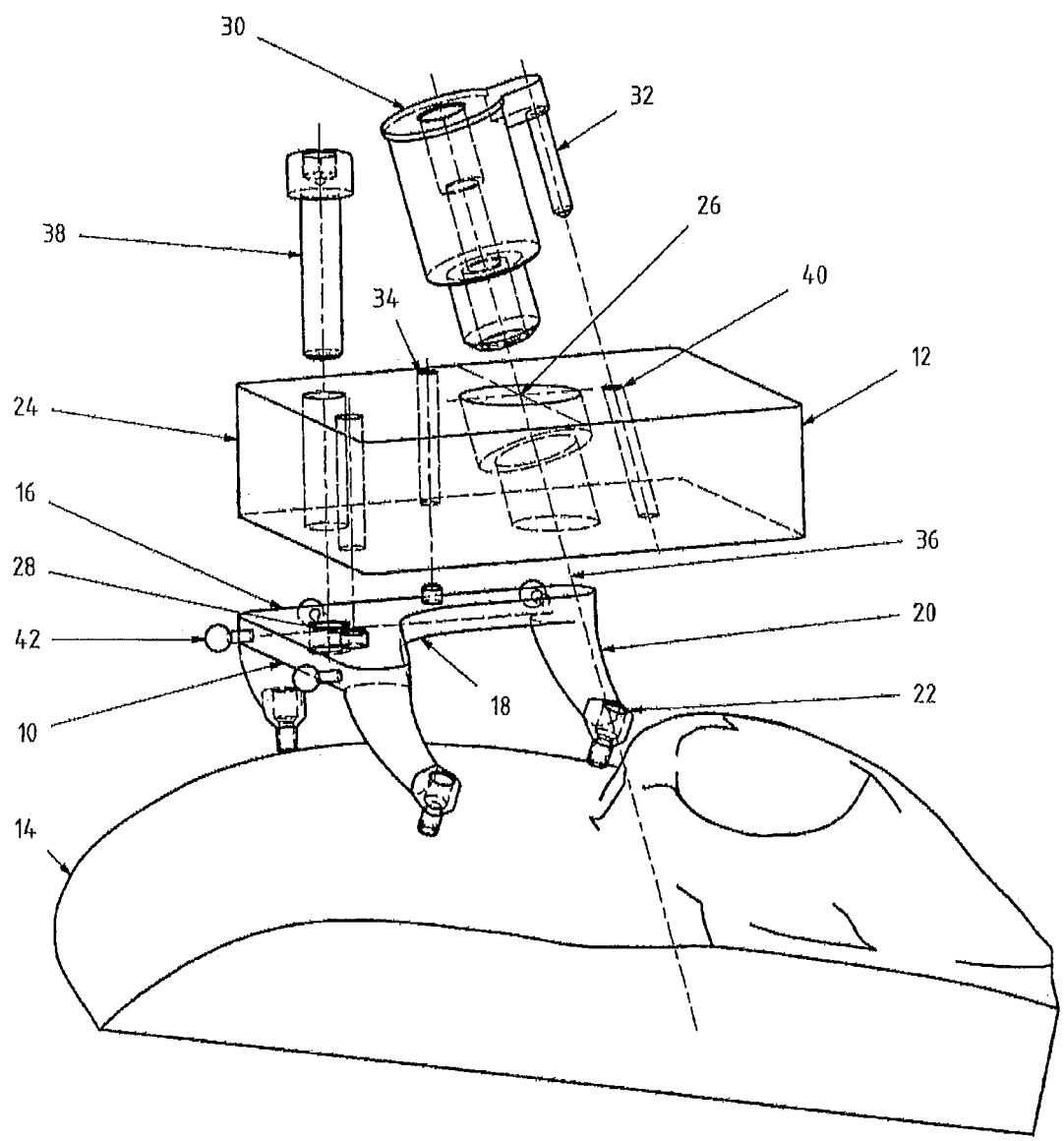

(51) Int. Cl.
*A61B 90/11* (2016.01)
*A61B 17/17* (2006.01)
*A61B 17/02* (2006.01)
*A61B 90/00* (2016.01)
*A61B 90/10* (2016.01)
*A61B 17/00* (2006.01)
*A61B 17/16* (2006.01)

(52) U.S. Cl.
CPC .............. *A61B 34/10* (2016.02); *A61B 90/11* (2016.02); *A61B 17/00234* (2013.01); *A61B 17/1695* (2013.01); *A61B 2090/101* (2016.02); *A61B 2090/103* (2016.02); *A61B 2090/363* (2016.02); *A61B 2090/3916* (2016.02); *A61B 2090/3983* (2016.02); *A61B 2090/3991* (2016.02)

(58) Field of Classification Search
CPC . A61B 17/1771; A61B 17/1739; A61B 17/17; A61B 2017/3405; A61B 2017/3407; A61B 2090/101; A61B 2090/103; A61B 2017/3403
USPC ........................................................ 606/130
See application file for complete search history.

(56) References Cited

U.S. PATENT DOCUMENTS

| | | | |
|---|---|---|---|
| 2011/0319913 A1 | 12/2011 | Labadie et al. | |
| 2013/0053867 A1* | 2/2013 | Gowda | A61B 17/00234 606/130 |
| 2016/0008074 A1* | 1/2016 | Glossop | A61B 90/11 606/130 |

FOREIGN PATENT DOCUMENTS

| | | |
|---|---|---|
| EP | 3 058 890 B1 | 10/2017 |
| WO | 2008/014261 A2 | 1/2008 |

OTHER PUBLICATIONS

Ramya Blachandran et al: "Minimally-Invasive, Image-Guided Cochlear Implantation for Pediatric Patients—Clinical Feasibility Study", Otolaryngol Head Neck Surg., Feb. 2, 2016, 7 pages.

Robert F. Labadie et al: "Customized, rapid-production microstereotactic table for surgical targeting: description of concept and in vitro validation", International Journal of Computer Assisted Radiology and Surgery, vol. 4, No. 3, May 1, 2009, pp. 273-280.

* cited by examiner

POSITIONING AID FOR SURGICAL PROCEDURES

CROSS REFERENCE TO RELATED APPLICATIONS

This application is the National Stage of PCT/DE2015/100227 filed on Jun. 8, 2015, the disclosure of which is incorporated by reference. The international application under PCT article 21(2) was not published in English.

The invention relates to a positioning aid for surgical procedures.

In surgical procedures on the cranium, as they are required for implantation of a cochlear implant, for example, until now the conventional method of procedure provided for uncovering of all relevant risk structures of the lateral cranium base, in order to guarantee its intactness. Subsequently, the middle ear is opened up between the facial nerve and the gustatory nerve, in order to thereby establish access to the inner ear.

To reduce the time expenditure, the operative risk, and the trauma, a minimally invasive approach is pursued. On the basis of pre-operative image data and planning data of the individual anatomy, access in the form of an individual puncture channel bore is placed from the cranium surface to the cochlea. In this regard, uncovering of the risk structures is not performed, nor is continuous tracking of patient and instruments. However, this requires highly precise implementation of planning data.

From U.S. Pat. No. 7,981,122 B2, a positioning aid is already known that is referred to as a micro-table among experts. The known positioning aid consists of a plate having a central bore that runs perpendicular to the surface of the plate, and legs that are affixed in pockets of the plate milled for the surgical procedure in accordance with planning data. The legs are kept on hand in graduated lengths, and it is determined by means of the depth of the pockets how far the legs project out of the plate. The plate can be spatially positioned and oriented on the cranial bone by way of the selected length of the legs and the depths of the pockets. It is simultaneously attached by way of ball markers anchored in the bone, which are disposed at ends of the legs that are at a distance from the plate.

Attachment of the legs in the pockets of the plate requires individual post-machining of the blanks. The ball markers that are anchored in the bone have a dual function. They function as registration markers and serve for anchoring the drilling template on the cranium. The design of the bone-anchored ball markers is therefore a compromise between the two requirements and leads to restricted precision.

Since the predetermined axis of the bore in the plate must be made to match the trajectory for the access to the cochlea, installation and adjustment of the positioning aid on the cranial bone is very time-consuming and tool-intensive. Also, sterile production is not guaranteed, so that additional sterilization must be carried out. In addition, this design offers only restricted mechanical strength.

The invention is based on the task of improving a positioning aid to the effect that it can withstand stress, and can be installed and removed precisely and quickly.

This task is accomplished, in the case of a positioning aid by means of
a carrier system and a template, wherein the carrier system consists of a carrier plate provided with a recess, and of supports, by means of which the carrier plate, over an operating field for surgical intervention, can be fixed to a cranial bone, and the template consists of a template plate which can be connected in a play-free manner to the carrier plate, said template plate having a guiding aperture, wherein the template plate consists of a blank in which the guiding aperture is arranged and oriented individually in accordance with predetermined coordinates by means of removal of material of the blank,
and the longitudinal central axis of the guiding aperture, when the carrier system and template are in the assembled state and the carrier system is fixed to the cranial bone, corresponds to a trajectory for an access to the operating field for the surgical intervention, wherein the longitudinal central axis of the guiding aperture is arranged eccentrically relative to the template plate, has an incline of the longitudinal central axis thereof which deviates from the vertical of the surface of the template plate, and the recess in the carrier plate is dimensioned to be of such a size that the guiding aperture in the template plate is not covered by the carrier plate even in the case of maximum eccentric arrangement.

Further developments and advantageous embodiments are discussed below.

The positioning aid according to the invention is structured in two parts and consists of a carrier system and a template. The carrier system can be reused and can be kept on hand in multiple sizes for different cranium sizes and shapes. The carrier system comprises a carrier plate having a recess. Here, a recess is understood to be a cavity that leads from one flat side of the carrier plate to the other and is enclosed, in whole or in part. A fully enclosed cavity preferably has a circular shape in a top view, while a partially enclosed cavity represents an indentation that can have a U-shaped, half-moon-shaped, sickle-shaped design, for example.

The template, in contrast, is specially produced for every procedure, from a blank that matches the selected carrier system. This can be a uniform body that consists of material that is present throughout, at first in the region of possible guiding apertures, into which body the guiding apertures are individually introduced in accordance with predetermined coordinates, by means of material removal such as boring, milling, for example. On the basis of previously created planning data for the surgical procedure, coordinates of a trajectory for access to the operating field for the surgical procedure are calculated. By means of transformation of these coordinates onto the template, the location and the orientation for the guiding aperture in the template plate are established, and the guiding apertures are carried out as drilled or milled holes. The template plate with the guiding aperture is a component that can be used only once, since the location and orientation of the guiding aperture relate to the individual anatomy of a patient and to the attachment location of the carrier system on the cranial bone.

Thus, first the carrier system can be positioned freely on the cranial bone, within limits, without having to pay attention to the trajectory for creating the access to the operating field. As a result, the carrier plate of the carrier system can be affixed closely to the cranial bone. In this regard, it is preferably oriented parallel to a tangential plane of the cranial bone, the contact point of which lies approximately in the center of the carrier plate. The resulting distances of the edges of the carrier plate from the cranial bone likewise allow short supports, and this has an advantageous effect on their mechanical stability. This is because deflection of the supports is less under the effect of force, and thereby greater precision of the orientation of the surgical tools is guaranteed.

Since the carrier system is prefabricated, it can be kept on hand in the sterile state. In the case of the template, only the guiding aperture has to be introduced into the template plate, and this can take place under sterile conditions. The time between the start of installation of the positioning aid until the start of the surgical procedure can be clearly reduced as compared with other systems.

Multiple variants are provided for the ends of the supports that face away from the carrier plate. The ends can either
a) have a hole raster, wherein the holes are passage sites and attachment sites of bone anchors, or
b) comprise a plurality of bone anchors, or
c) carry mandrel-like pins that can be braced relative to the cranial bone by means of bone screws.

By means of these possible methods of attachment, the carrier system can be anchored on the cranial bone in such stable manner that the required dimensional accuracy for use of the surgical tools is guaranteed, and the forces that occur during the procedure can also be absorbed without changing the position of the positioning aid.

It can be provided that the supports comprise planned breaking points.

As a result, it is possible to quickly remove the carrier system even without loosening the anchors in the cranial bone.

Alternative means can be provided for precise orientation of the template plate on the carrier plate. Thus, the possibility exists that
a) pins are disposed on one of the two plates, namely the carrier plate or the template plate, and recesses for accommodation of the pins are disposed on the other plate, in each instance, namely the template plate or the carrier plate, and the pins of the one plate are inserted into the recesses of the other plate in the installed state, or
c) recess for accommodation of pins are present on both plates, namely both on the carrier plate and on the template plate, and in the installed state, pins are inserted into both recesses of the plate, in each instance, and that the plates are braced against one another.

This can be implemented in known manner, by means of screws, springs or clamps.

Both variants allow a play-free connection between the template plate and the carrier plate.

The pins or recesses can be present at least in duplicate, in each instance, and can be structured differently and/or disposed asymmetrically.

In the case of skillful distribution over the carrier system, two pins or recesses are already unique. If they are additionally also structured differently, for example have different diameters or cross-sectional shapes, they only fit together in one possible orientation. Alternatively, three asymmetrically disposed pins or recesses are suitable.

In this way, the result is achieved that the template plate can be connected with the carrier plate only in a single possible orientation. Incorrect orientations are thereby reliably prevented.

Preferably, a replaceable cylindrical tool-guiding body is disposed in the guiding aperture.

The tool-guiding body can be dimensioned and removed in a manner specifically for Use of surgical tools, in such a manner that room is guaranteed for introduction of an implant.

Preferably, the tool-guiding body has a stop for depth adjustment of a tool.

In this way, the penetration depth of a surgical tool can automatically be restricted.

Furthermore, the tool-guiding body can have an anti-twist device in the form of a pin that engages into a recess disposed next to the guiding aperture in the template plate.

In this way, the tool-guiding body is prevented from being twisted when a torque is exerted.

The recess in the carrier plate and the guiding aperture in the template plate can have a slit that is open toward the outside or a U-shaped open shape.

In this way, it is possible to supply cables to the positioning aid from the side when inserting an implant.

Furthermore, registration markings can be disposed on the carrier system, or the carrier system itself or parts of it can themselves be structured as registration markings.

The registration markings allow spatial detection of the carrier system affixed to the cranial bone relative to the anatomy of the cranium of the patient within the scope of three-dimensional imaging. Precise spatial detection of the carrier system affixed to the cranial bone in turn is a prerequisite for transfer of the coordinates of the guiding aperture in the template plate, so that its axis matches the trajectory for access to the operating field after installation of the template plate on the carrier plate.

Figure 2:
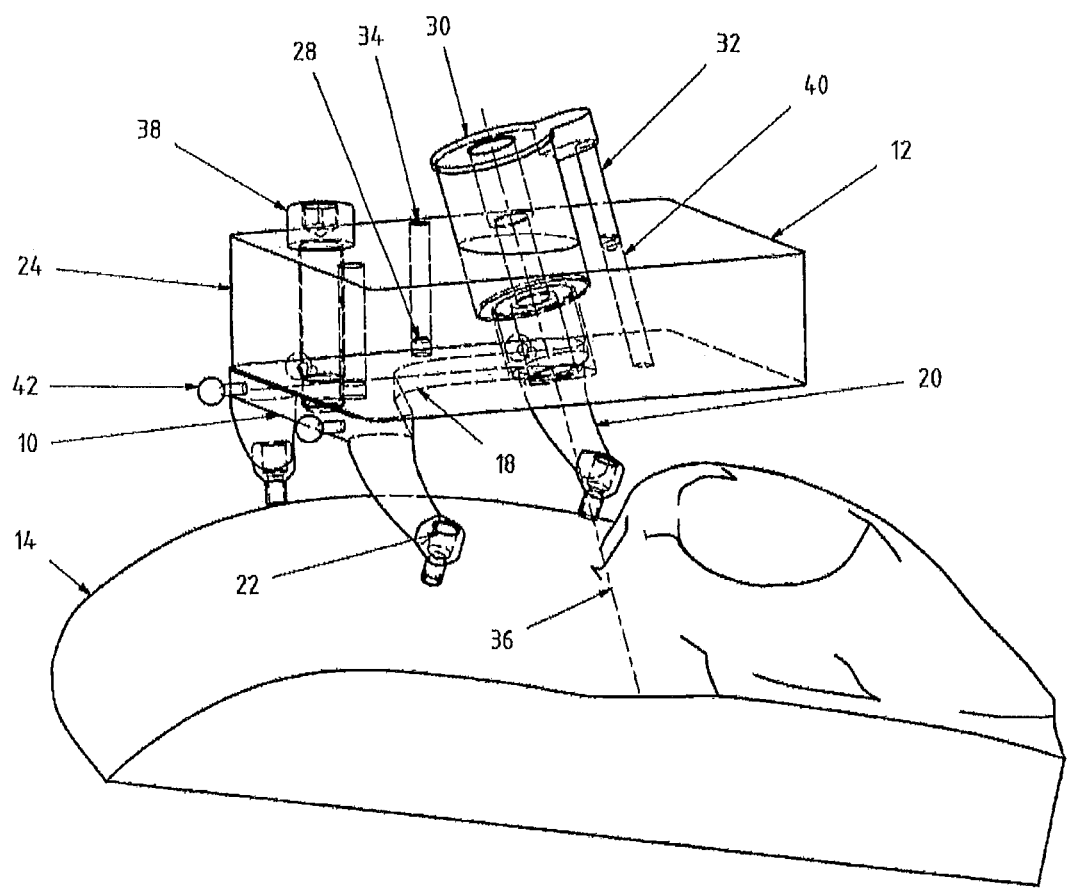

In the following, the invention will be explained using an exemplary embodiment, which is represented in the drawing. This shows:

FIG. 1 a perspective view of a positioning aid in an exploded representation, and FIG. 2 a perspective view of the positioning aid in the installed state.

The positioning aid for surgical procedures shown in FIGS. 1 and 2 comprises a carrier system 10 and a template 12. The carrier system 10 consists of a carrier plate 16 provided with a recess 18, and supports 20, by means of which the carrier plate 16 is attached to a cranial bone 14 above an operating field for the surgical procedure. The template 12 consists of a template plate 24 having a guiding aperture, which plate can be connected with the carrier plate 16 in play-free and shape-fit manner. The longitudinal central axis 36 of this guiding aperture 26 can be disposed and oriented individually, according to predetermined coordinates, on an access to the operating field for the surgical procedure. It can therefore, as shown in the exemplary embodiment, be disposed eccentrically relative to the template plate 24, and have an inclination of its longitudinal central axis 36 that deviates from the perpendicular to the surface of the template plate 24.

The recess 18 in the carrier plate 16 is dimensioned to be so large that the guiding aperture 26 in the template plate 24 is not covered by the carrier plate 16 even in the case of maximally eccentric placement. There are supports 20 at three locations of the flat side of the carrier plate 16 that faces the cranial bone 14, with which supports the carrier plate 16 is supported on the cranial bone 14 and can be fixed in place. At the ends, there are feet 22 having mandrel-like pins. The feet 22 support themselves on the skin or the cranial bone 14. The carrier plate 16 is braced against the cranial bone by means of a bone screw.

Close to the edges of the carrier plate 16, there are pins 28 that project toward the template plate 24 and align with recesses 34 of the template plate 24. The pins 28 and recesses 34 are disposed asymmetrically and permit the template plate 24 and carrier plate 16 to be put together only in a single one of three angle positions that appear possible at first. Here, the template plate 24 is fixed in place with the carrier plate 16 by means of three screws 38, which are screwed onto threads of the pins 28. The template plate 24 and the carrier plate 16 are oriented without play relative to one another by means of the pins 28 and recesses 34.

Above the guiding aperture 26 in the template plate 24, there is a tool-guiding body 30 that serves for guiding and holding a surgical tool. An anti-twist device in the form of a pin 32 is disposed on the tool-guiding body 30, which pin engages into a recess 40 of the template plate 24 when the tool-guiding body 30 is inserted into the guiding aperture 26.

While the positioning pins are shown in an exploded representation in FIG. 1, the individual components are shown in the installed state in FIG. 2.

In the preparation for a surgical procedure, first the anatomy of the cranium of a patient is recorded by means of imaging methods, and thereupon the surgical procedure is planned. A component of this planning is orientation of a common axis for a drilled or milled hole in the cranial bone and further access to the operating field. A carrier system 10 is selected on the basis of the size and shape of the cranium, which system is fixed in place on the cranial bone 14. The registration markings 42 affixed on the carrier system 10, which markings have the greatest possible distance from one another, serve for determining the spatial placement of the carrier system 10 attached to the cranial bone 14 relative to the anatomy of the cranium of the patient. These registration markings 42 are represented more clearly than the other components of the carrier system 10 within the scope of a subsequent three-dimensional imaging of the patient, and thereby facilitate detection of the coordinates of the carrier system 10. The coordinates of the carrier system 10 as well as of the trajectory for access to the operating field are transferred to the template plate 24. The location and the inclination for the guiding aperture 36 in the template plate 24 are determined from this, and this opening is produced. Afterward, the template plate 24 is fixed in place on the carrier plate 16 and the tool-guiding body 30 is inserted.

With this, the mechanical prerequisites for precise guidance of the surgical tool for opening up the cranial bone, advancing to the operating field, and inserting the implant have been completed.

REFERENCE SYMBOL LIST 10 carrier system
12 template
14 cranial bone
16 carrier plate
18 recess
20 supports
22 feet
24 template plate
26 guiding aperture
28 pins
30 tool-guiding body
32 pin
34 recesses
36 longitudinal central axis
38 screws
40 recess
42 registration markings

The invention claimed is:

1. A positioning aid for a surgical procedure on a patient, comprising
a carrier system; and
a template;
wherein the carrier system comprises a carrier plate with an opening or a recess and with supports to fixate the carrier system to a cranial bone over an operating field for surgical intervention;
wherein the carrier plate has first and second ends with the opening or the recess disposed between the first and second ends;
wherein the template comprises a template plate connected in a play-free manner to the carrier plate so as to extend beyond at least one of the first and second ends of the carrier plate, said template plate having a guiding aperture, which can be created and oriented by means of removal of material from a blank template plate, said guiding aperture being configured at a location and orientation relative to the patient and to an attachment location of the carrier system in accordance with predetermined coordinates based on calculations from planning data for the surgical procedure on the patient;
wherein the longitudinal central axis of the guiding aperture, when the carrier system and template are in the assembled state and the carrier system is fixed to the cranial bone, corresponds to a trajectory for an access to the operating field for the surgical intervention; and
wherein the longitudinal central axis of the guiding aperture is arranged eccentrically relative to the template plate and offset from a center point of the recess or the opening of the carrier plate, said longitudinal central axis of the guiding aperture having an incline which deviates from the vertical of the surface of the template plate, the recess or the opening in the carrier plate being dimensioned to be of such a size that the guiding aperture in the template plate is not covered by the carrier plate even in a case of maximum eccentric arrangement.

2. The positioning aid according to claim 1, wherein the supports, at ends thereof facing away from the carrier plate, either
a) have a hole pattern, wherein the holes are penetration and fixing locations of bone anchors or
b) comprise a plurality of bone anchors or
c) bear mandrel-type pins which can be tightened to the cranial bone by means of bone screws.

3. The positioning aid according to claim 1, wherein the supports comprise predetermined breaking points.

4. The positioning aid according to claim 1, wherein
a) pins are arranged on one of the carrier plate or the template plate, and recesses for receiving the pins are arranged on the respective other one of the template plate or the carrier plate, and in the mounted state the pins of one plate fit into the recesses of the other plate, or
b) on both the carrier plate and the template plate, there are recesses present for receiving pins, and in the mounting state pins respectively fit into both recesses of the plates and the plates are tightened against one another.

5. The positioning aid according to claim 4, wherein at least two pins or recesses are respectively present and are designed differently from each other and/or are arranged asymmetrically.

6. The positioning aid according to claim 1, wherein an exchangeable cylindrical tool-guiding body is arranged in the guiding aperture.

7. The positioning aid according to claim 6, wherein the tool-guiding body has a stopper for the depth adjustment of a tool.

8. The positioning aid according to claim 1, wherein the tool-guiding body has an anti-rotation device which engages in a recess arranged beside the guiding aperture in the template plate.

9. The positioning aid according to claim 1, wherein the recess in the carrier plate and the guiding aperture in the template plate have an outwardly leading slot or a U-shaped open form.

10. The positioning aid according to claim 1, wherein registration markings are arranged on the carrier system, or the carrier system itself or parts thereof are designed as registration markings.

* * * * *